United States Patent
Neumann (10) Patent No.: US 6,523,298 B2
(45) Date of Patent: *Feb. 25, 2003

(54) CAPSICUM BASED PESTICIDE AND METHOD OF USE

(75) Inventor: Robert Heinz Neumann, 1530 Arroyo, San Carlos, CA (US) 94070

(73) Assignee: Robert Heinz Neumann, San Carlos, CA (US)

(*) Notice: Subject to any disclaimer, the term of this patent is extended or adjusted under 35 U.S.C. 154(b) by 32 days.

This patent is subject to a terminal disclaimer.

(21) Appl. No.: 09/747,225

(22) Filed: Dec. 22, 2000

(65) Prior Publication Data

US 2001/0054248 A1 Dec. 27, 2001

Related U.S. Application Data

(63) Continuation-in-part of application No. 09/374,548, filed on Aug. 12, 1999, now abandoned, which is a continuation of application No. 08/871,004, filed on Jun. 6, 1997, now Pat. No. 5,937,572.

(51) Int. Cl.[7] ............................................... A01M 1/20
(52) U.S. Cl. ..................................................... 43/132.1
(58) Field of Search ........................................ 43/132.1

(56) References Cited

U.S. PATENT DOCUMENTS

| 312,270 A | | 2/1885 | Hoag | |
|---|---|---|---|---|
| 3,793,763 A | * | 2/1974 | Griffin et al. | 43/129 |
| 4,889,710 A | * | 12/1989 | Hagarty | 424/45 |

(List continued on next page.)

OTHER PUBLICATIONS

Download from Hot Pepper Wax, Inc., HotpepperWax–Products, Jan. 8, 2001, 16 pages.
Toxicological Aspects of White Mineral Oils and Petrolatums, Penreco Technical Series, 2 pages.
Download form www.Kalsec.com, Products, Capsicum Oleoresins, Jun. 28, 2000, 3 pages.

(List continued on next page.)

Primary Examiner—Charles T. Jordan
Assistant Examiner—Jordan M. Lofdahl
(74) Attorney, Agent, or Firm—Ray K. Shahani, Esq.

(57) ABSTRACT

A method for exterminating existing infestations of ants, termites, insects or other living organisms in structures, soils and other materials using a capsicum-containtg killing solution in either a liquid or vapor form, including the steps of delivering the killing solution to the infested portions of the structure, and contacting the termites, insects or other living organisms forming the infestation. The method obviates the need for toxic or environmentally unsafe chemical compounds, and capsicum is readily available and economical. More importantly, the novel pesticide and method of use of the present invention is highly effective against termites in dry areas, wet areas, inaccessible and exposed areas, including around and under foundations, in ceiling and in wall portions of structures. Boring small holes into the structure, from either the inside or the outside and penetrating into the interior wall, ceiling and foundation spaces will allow the capsicum based killing solution to be pumped directly therein. Additionally, the killing solution can be applied underneath vapor barriers into the soil to eliminate nematodes in soil prior to other agricultural activities.

20 Claims, 3 Drawing Sheets

U.S. PATENT DOCUMENTS

| | | |
|---|---|---|
| 5,027,546 A | 7/1991 | Tallon |
| 5,063,706 A * | 11/1991 | Aki et al. ................. 43/124 |
| 5,165,199 A | 11/1992 | Tallon |
| 5,240,708 A | 8/1993 | Plummer et al. |
| 5,309,669 A * | 5/1994 | Jackson ................. 43/124 |
| 5,361,533 A * | 11/1994 | Pepper ................. 43/124 |
| 5,390,440 A * | 2/1995 | Mihealsick ............. 43/124 |
| 5,419,077 A * | 5/1995 | Tombarelli ............. 239/121 |
| 5,466,459 A | 11/1995 | Wilson |
| 5,489,066 A * | 2/1996 | Oldham ................. 239/722 |
| 5,514,779 A | 5/1996 | Broakaert et al. |
| 5,525,597 A | 6/1996 | Hainrihar et al. |
| 5,542,207 A | 8/1996 | Morris, Sr. |
| 5,599,803 A | 2/1997 | Hainrihar et al. |
| 5,711,953 A | 1/1998 | Bassett |
| 5,937,572 A | 8/1999 | Neumann |
| 6,047,496 A * | 4/2000 | Leitner et al. ............. 43/125 |

OTHER PUBLICATIONS

Penreco, Drakeol 7 light Mineral Oil NF—Product Spcification, 5 pages.

Download from www.hort.purdue.edu.com, Peppers: History and Exploitation of a Serendipitous New Crop Discovery, W. hardy Eshbaugh, May 23, 1997,11 pages.

Long–Awaited Nonchemical Alternatives to Drywood Termite Control Study Completed Pest Control Operator of California, Summer 1996,4 pages.

Helix (TM) Xtra, Syngentra product label for seed treatment, 2 pages.

* cited by examiner

CAPSICUM BASED PESTICIDE AND METHOD OF USE

RELATED APPLICATIONS

This application a continuation in part of U.S. patent application Ser. No. 09/374,548 filed Aug. 12, 1999 now abandoned, which is a continuation of U.S. Pat. No. 5,937,572 issued Aug. 17, 1999, application Ser. No. 08/871,004 filed Jun. 6, 1997.

FIELD OF THE INVENTION

The present invention relates generally to pesticides and methods for extermination of undesirable living organisms. More particularly, the present invention is a novel compound and method for exterminating termites in and around residential and commercial foundations and in wall and ceiling structures and elsewhere, using an aqueous solution comprising capsicum, a chemical non-toxic to humans and highly active against living insects including termites and ants.

BACKGROUND OF THE INVENTION

Presently, much is known about capsicum. A current internet site located on the world wide web at http://neptune.netimages.com/%7Echile/science.html provides a great deal of background information. Peppers are members of the genus Capsicum, and the family Solanaceae, which include eggplant and tomatoes. The name Capsicum comes from the Greek kapto, which means "to bite".

It is estimated that there are at least 26 species of peppers categorized at present, most of which are found in the wild. There are five species of domesticated peppers:(1) annuum, from "annual; this includes most of the common peppers found in markets including bell peppers, jalapeños and New Mexican; (2) *baccatum*, from "berry-like"; these are the aji peppers found commonly in South America; (3) *chinense*, meaning "from China"; this includes the famous habanero, Scotch Bonnets, etc.; (4) *frutescens*, meaning "brushy" and are the tabasco peppers; and (5) *pubescens*, from "hairy"; these are the South American rocoto peppers. References to annuum species often include the pod type. Due to easy inbreeding between *annuum, chinense* and *frutescens*, there are hundreds of different varieties found throughout the world. All peppers originated in the New World. The origin seems to be in the area of Bolivia and Paraguay in South America. Wild peppers were spread by birds, who are apparently unaffected by the heat of the fruit.

Many varieties of the Capsicum species are not hot, or pungent. Most paprikas grown in Europe and bell peppers grown in the US have little or no pungency. These varieties are used fresh, or often used to color other foods. The wilder varieties, on the other hand, range from mildly to extremely pungent. This is entirely due to the substance capsaicin, or, actually, a group of similar substances called capsaicinoids. Pure capsaicin, or 8-methyl-n-vanillyl-6-nonenamide, is a whitish powder which is soluble in alcohol but insoluble in cold water, which is why drinking water to help alleviate the burning won't work. The capsaicinoids are unique compared to other "spicy" substances such as mustard oil (zingerone and allyl isothiocyanate), black pepper (piperine) and ginger (gingerol) in that capsaicin causes a long-lasting selective desensitization to the irritant pain by repeated doses of a low concentration or a single high concentration dose.

The use of capsicum in an aqueous solution for exterminating termites is completely unknown. Numerous other uses for chile peppers have been patented. U.S. Pat. No. 5,217,708 teaches an aerosol lachrymator formulation having all natural pepper extracts as the active ingredients. The lachrymator formulations are useful in self-defense devices. The formulations are non-toxic and have a broader spectrum of activity than man-made lachrymators. These aerosol formulations rely on a carbon dioxide propellant.

Numerous applications of capsicum for medicinal or therapeutic purposes, such as in cough drop formulations, analgesics, thermo slimming cosmetic compositions, ache and pain compounds and arthritis compositions are found in U.S. Pat. Nos. 4,980,169, 4,931,277, 4,702,916, 4,795,638, 4,592,912 and 4,271,154. These applications are unrelated to the present invention.

Numerous applications include the use of capsicum to discourage growth of living organisms. U.S. Pat. No. 5,226,380 teaches a covering material for underwater objects such as boat hulls or water intake pipes. The covering includes a waterproof coating such as adhesive or paint containing capsicum derivatives such as cayenne pepper or oleoresin capsicum, with the coating applied to the outer surface of the object to be protected, to repel marine organisms which might otherwise attach themselves to the object.

U.S. Pat. Nos. 5,599,803 and 5,525,597 teach insecticidal compositions, comprising normally-employed insecticides but comprising also an effective activity-enhancing amount of capsaicin or other capsaicinoid, especially in the form of capsicum, which exhibit synergistic effects against numerous insects, including especially bud worms, boll worms, cabbage loopers, army worms, beet army worms, and beetles, and are especially effective on cotton, soybeans, common garden vegetables, and flowers, when sprayed on the insect or its habitat, especially as an aqueous solution, suspension, or emulsion. Larger crop stands may be effectively treated by aerial spraying from the usual crop-dusting airplane.

U.S. Pat. No. 5,514,779 teaches biocidal proteins capable of isolation from seeds have been characterized. The proteins have an amino acid sequence containing the common cysteine/glycine domain of Chitin-binding Plant Proteins but show substantially better activity against pathogenic fungi, a higher ratio of basic amino acids to acidic amino acids, and/or antifungal activity which results in increased hyphal branching. Antimicrobial proteins isolated from Amaranthus, Capsicum, Briza and related species are provided. The proteins show a wide range of antifungal activity and are active against Gram-positive bacteria. DNA encoding the proteins may be isolated and incorporated into vectors. Plants may be transformed with this DNA. The proteins find agricultural or pharmaceutical application as antifungal or antibacterial agents. Transgenic plants expressing the protein will show increased disease resistance.

U.S. Pat. No. 5,240,708 teaches a composition and method for spraying an area to inhibit web growth and discourage spiders, other insects or the like from returning to the sprayed area. The solution includes liquid soap that is blended with oil of anise and coriander oil. Capsicum is then added and completely blended in the soap mixture. The mixture is blended with an acetic acid solution to form the solution.

U.S. Pat. No. 5,544,304 teaches a composition for repelling birds, the composition having as active ingredients finely divided dried pepper from pungent fruits of plants of the genus Capsicum and finely divided dried garlic and typically being diluted by inert, finely divided mineral material or water for application to the earth surface or to growing plants to repel birds given to eating seeds, plants, vegetables, and fruits.

With regard to the prior art teaching the use of capsicum as an adjunct ingredient to an insecticidal composition, all of these compositions include the use of other, toxic, non-capsicum based chemicals. The use of capsicum therein is as an adjunct, not as a replacement. The use of a solution of capsicum alone in water is neither taught nor suggested in any of the relevant prior art available.

In the generally well known and accepted prior art for extermination of termites and other insect infestations, little is known regarding the availability of safe, efficacious and non-toxic to humans formulations or methods. Methyl bromide is a common chemical which does damage to the ozone layer, is volatile and is very toxic to humans. The gas or liquid is injected directly into soil for extermination of, for example, undesirable crop insects. At present, however, the use of methyl bromide is being discontinued due to changes in the law. However, other chemicals also have similar drawbacks—they are either damaging to the environment or are toxic to humans, or any combination of the two.

One non-chemical approach to termite extermination is taught by U.S. Pat. No. 5,165,199 issued Nov. 24, 1992 to Tallon. This invention concerns a non-toxic method of exterminating dry wood termites, fleas, roaches, ants, weevils and the like by utilizing an inert freezing liquid such as liquid nitrogen as the killing agent. The liquid nitrogen is inserted so as to envelop the colony of objectionable organisms until the environment is reduced to a temperature of at least zero degrees Fahrenheit and maintained at that temperature for between 2 to 5 minutes. Unfortunately, this method requires transportation of heavy, compressed gas-type cylinders for containing the freezing cryogenic liquid. Furthermore, the use of such materials is not only expensive but dangerous, and an accident operating the tanks and transfer equipment can cause significant bodily injury to operators and others.

Thus, while it is known that capsicum and pepper-extract containing formulations exhibit properties which repel animals such as ocean crustaceans, crop and plant insects, birds, etc., there is no reference in the prior art to the use of such formulations for exterminating termites or for clearing existing insect and pest infestations from soil or structures.

ADVANTAGES AND SUMMARY OF THE INVENTION

Therefore, it is an advantage and an objective of the present invention to provide a safe and economical method for the extermination of termites and/or other insect and pest infestations in soil, in or around foundations of houses and buildings, or in or around walls, ceilings, patios, gazebos, walkways or other infested parts of structures.

It is a further advantage and objective of the present invention to provide methods and killing solutions for exterminating termites, insects, and other pests in hard to reach, generally inaccessible areas as well as in visible, surface, accessible areas or portions of a structure.

It is a further advantage and objective of the present invention to provide a formulation, solution, emulsion, solid or gas for applying to soil, foundations of houses and buildings, walls, ceilings or other parts of structures for exterminating termites, insects or other pest infestations.

It is yet a further advantage and objective of the present invention to provide a formulation and method of killing all types of termites, all types of ants, and all other types of agricultural pests including aphids, boll weevils, cabbage seed pod weevils, etc.

In summary, the present invention is a method for exterminating insects and other undesirable living organisms living in a structure or material including the steps of preparing an aqueous solution having a predetermined amount of capsicum. By contacting any living organism such as termites, spiders, ants, etc. with an aqueous solution containing any operable amount of capsicum, the cells of the body part of the insect or other living organism in contact with the killing solution will be disrupted and the organism will be killed. Spraying and injecting the killing solution into walls, ceilings, foundations, soil around foundations and tree stumps, etc., will rid those areas completely of an existing infestation.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Figure 1:
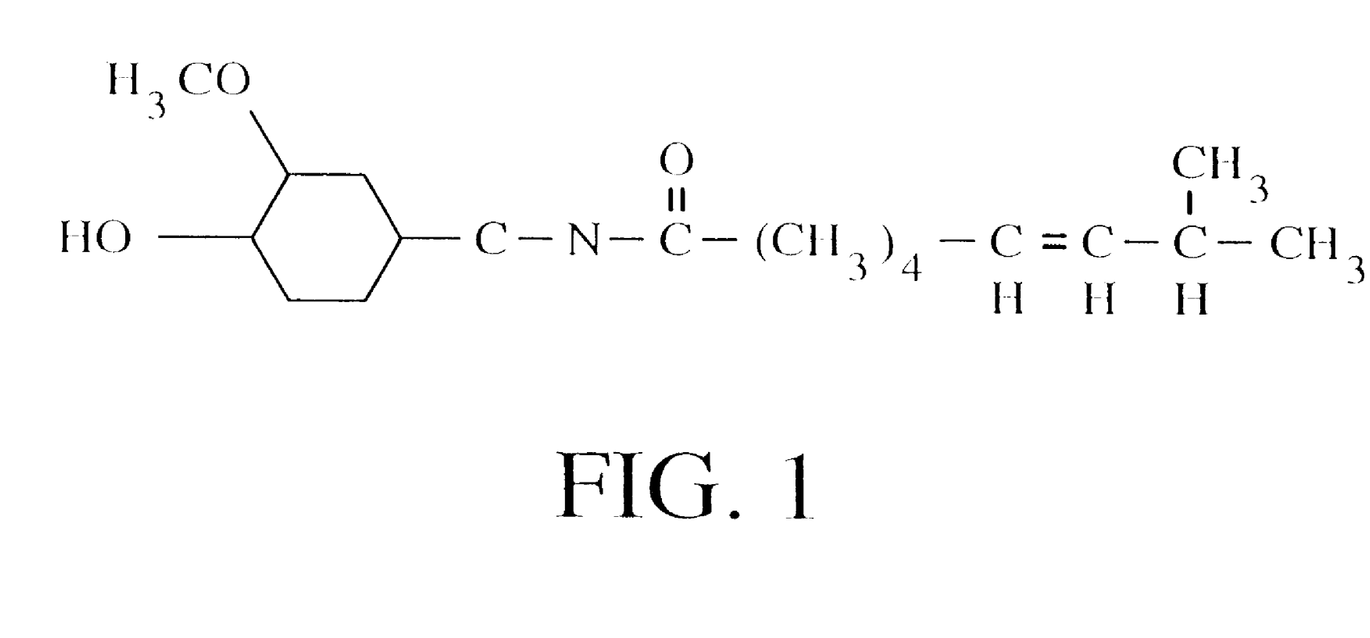
FIG. 1 is the chemical structure of capsaicin.

FIG. 1 is the chemical structure of capsicum or capsaicin 100. Capsaicin, also known as N-vanillyl-8-methyl-6-(E)-noneamide, is the most pungent of the group of compounds called capsaicinoids isolated from peppers. It is sparingly soluble in water, but very soluble in fats, oils and alcohol. The second most common capsaicinoid is Dihydrocapsaicin. Capsaicin and Dihydrocapsaicin together make up 80–90% of the capsaicinoids found in the fruit. In *C. annuum* the total capsaicinoid content ranges from 0.1 to 1.0%, and the capsaicin:dihydrocapsaicin ratio is about 1:1. In *C. frutescens*(Tabasco peppers) the total content ranges from 0.4–1.0% with the ratio around 2:1.

The minor capsaicinoids include Nordihydrocapsaicin [Dihydrocapsaicin with $(CH2)5$ instead of $(CH2)6$], Homocapsaicin [Capsaicin with $(CH2)5$ instead of $(CH2)4$], and Homodihydrocapsaicin [Dihydrocapsaicin with $(CH2)7$ instead of $(CH2)6$]. The pungencies of these five pure compounds in Scoville Units (SU) are as follows:

| Compound | Pungency × 100,000 SU |
| --- | --- |
| Capsaicin | 160 |
| Dihydrocapsaicin | 160 |
| Nordihydrocapsaicin | 91 |
| Homocapsaicin | 86 |
| Homodihydrocapsaicin | 86 |

Govindarajan, VS and Sathyanarayana, MN; Capsicum—Production, Technology, Chemistry and Quality. Part V. Impact on Physiology, Nutrition and Metabolism; Structure, Pungency, Pain and Desensitization Sequences, *Crit. Rev. Food Sci. Nutr.* 29, 435. 1991 There are also homologs and analogs, such as with straight alkyl chains, that exist in nature.

Quantitation of capsicum amount in solutions is an important tool in manufacture. Following is a high performance liquid chromatography (HPLC) method for capsaicin determination: 25 g ground red pepper extracted in 200 mL 95% ethanol at 65–75 C. for 5 hours, allow to settle, decant, and cool to 20 C. 50 microliters injected from a 100 microliter Hamilton LC syringe via a Waters U6K injector into a Waters HPLC system with a 10 micron micro-Bondapak C18 column and a Bondapak C18/Corasil guard column and a UV detector set at 280 nm. HPLC operated isocratically with a Waters 660 solvent programmer using a mobile phase of 40:60 v/v acetonitrile:water (1% acetic acid) at 1.5 ml per minute. Quantitation done using commercially available N-vanillyl-n-nonamide as an external standard. Hoffman, Patrick G.; Lego, Mary C.; and Galetto, William G. "Separation and Quantitation of Red Pepper Major Heat Principles by Reverse-Phase High-Pressure Liquid Chromatography" J. Agric. Food Chem. 1983, vol. 31 pp 1326–1330.

Experimentally, it has been found that capsicum containing aqueous solutions are effective for exterminating drywood, subterranean and dampwood termites, wood boring beetles, fungi of various types, mosquitoes, flies, earthworms and spiders. Using a hot, pungent variety of a typical pepper such as *C. annuum* with an average of about 0.5% capsaicin content, a solution containing as little as 10 grams of ground pepper in about 454 mL water will contain about 0.01% capsaicin, sufficient for most applications disclosed herein. Therefore, optimally an aqueous solution will contain between about 0.00001% and about 1.0% by weight capsaicin or capsicum.

The solution can be formed using ground peppers mixed directly into water. The peppers may be dried or fresh, chopped or ground or powdered. To increase solubility of certain preparations of chilli peppers, the temperature of the water can be raised to room temperature or above. Electric or manual mixers can be employed, and it will be understood that a certain, predetermined time constant related to the solubility of the pepper material in the aqueous solution will be a factor to consider in preparing the solution.

Figure 2:
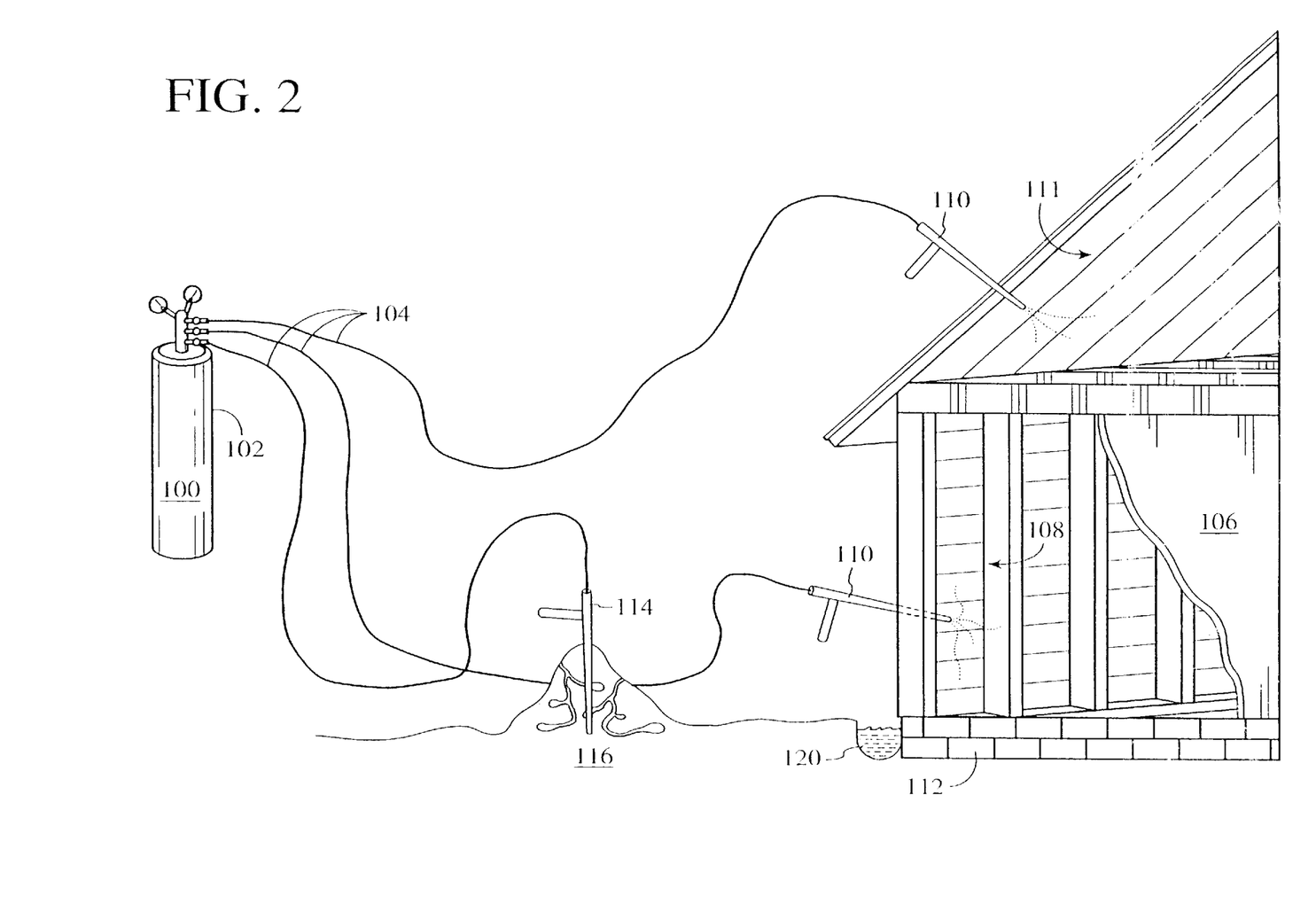
FIG. 2 is a representative drawing of methods of the preferred embodiments of the invention of the present invention.

FIG. 2 is a representative drawing of a method of the preferred embodiment of the invention of the present invention. The killing solution 100, an aqueous solution containing capsicum is stored in a reservoir 102. One or more supply lines 104 extends from the nozzle of the reservoir 102 to a point of application. It will be understood that the reservoir 102 of killing solution 100 may be pressurized, in which case associated air compressor, adjunct cylinders of compressed gas propellant(s) and/or other equipment may be required.

Directing the killing solution 100 into a structure 106 is extremely effective. Known techniques of spraying existing pesticides into residential and commercial structures can effectively be used with the killing solution of the present invention.

An initial approach, depending upon the sites of infestation, include injecting liquid solution into spaces between joists in a wall 108 and in or around ceiling spaces 111. The wall spaces are familiar a breeding grounds for termites, spiders, etc. Small holes can be bored into the walls 108 or other infested material or spaces at any point in the walls, either on the inside or the outside of the structure 106, and the capsicum solution can be injected therein in a liquid, aerosol, droplet, vapor, foam or other form.

As mentioned, the killing solution can be injected into the structure in a liquid or vapor form. It can be pumped straight in, through a nozzle of some sort 110, sprayed or vaporized by pumping through an aerosol-forming nozzle. It can also be boiled into steam containing active amounts of capsaicin and transported in pressurized lines to the target areas. By directing the liquid into individual joist-defined sections of a wall structure, the entire wall structure can be effectively treated. Any portion of a residential structure or a commercial structure can be effectively treated in this manner.

FIG. 2 also shows the method of exterminating an infestation located in soil 116, such as adjacent a foundation portion 112 of a structure 106. An injection tube 114 can be placed in the soil 116 adjacent the foundation portion 112, and killing solution can be pumped therethrough, at essentially any pressure (e.g., trickle rate) or in essentially any form (e.g., liquid, vapor). Spiders, earthworms, insect larvae, etc., when contacted with the killing solution will immediately be killed. By spraying a surface area with a larger volume of solution, the soil can be penetrated as deeply as desired, and additional injection nozzles used can be added. An alternative treatment method includes digging an irrigation trench 120 around the foundation 112 of the structure 106, and flooding the trench 120 with killing solution will result in saturation of a large volume of surrounding soil or other material, resulting in complete extermination of the existing infestation.

It will be understood, therefore, that alternative methods of exterminating soil or other portions of structure or materials include injecting the killing solution, in either a vapor, spray, mist or liquid form, between some barrier component and the infestation. Said barrier component could be a plastic sheet or rubber tarp, net mesh, etc., and will be known to those skilled in the art. Additionally, the killing solution can be applied underneath vapor barriers into the soil to eliminate nematodes and other undesirable insects or pests in soil prior to or concurrent with other agricultural activities.

Figure 3:
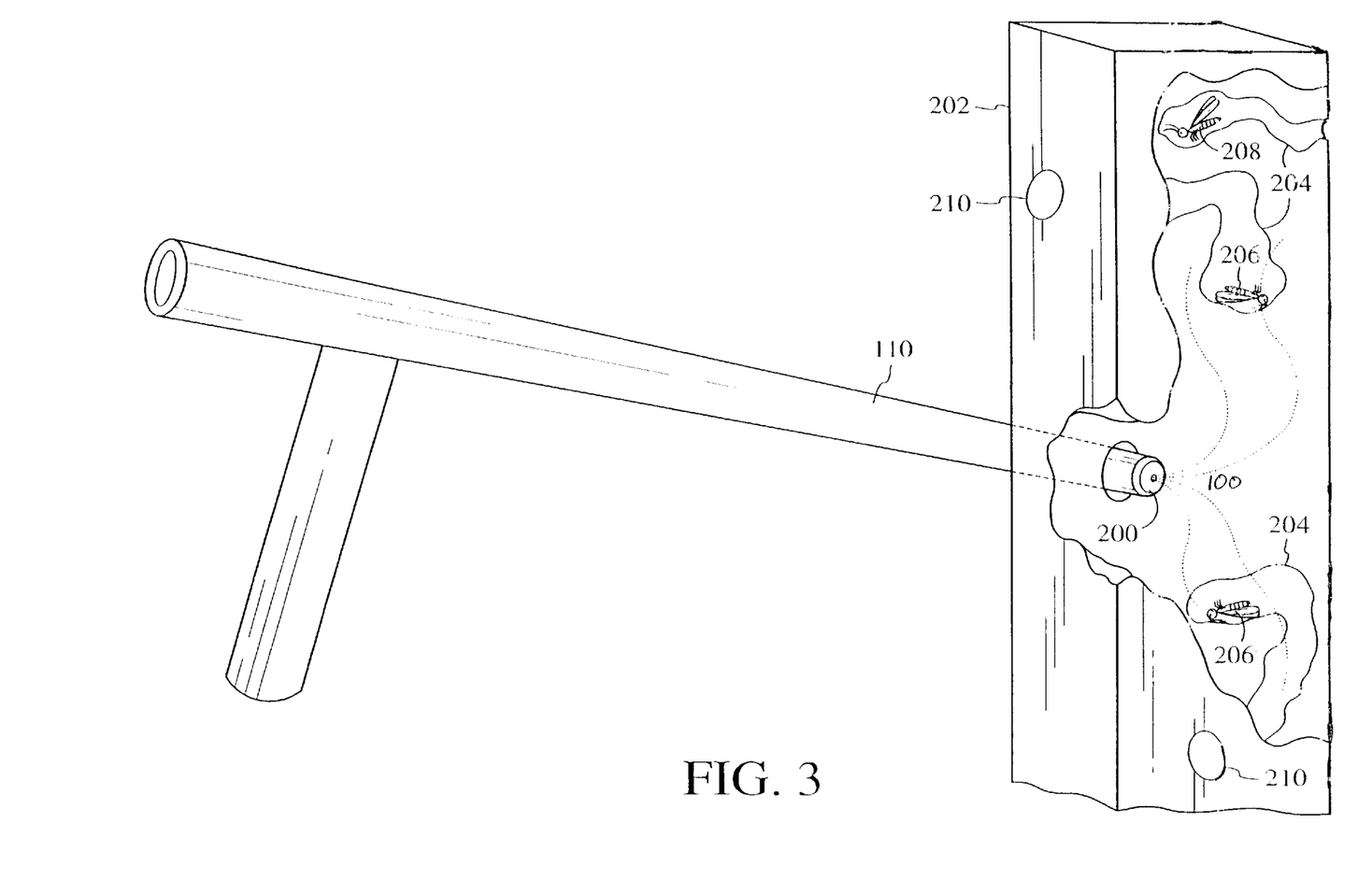
FIG. 3 is a representative drawing of another method of the preferred embodiments of the invention of the present invention.

FIG. 3 is a representative drawing of another method of the preferred embodiments of the invention of the present invention. In this drawing, a nozzle 110 is shown with its distal nozzle end 200 inserted into small injection ports 210 or other openings in a section of wood 202 or other infested material. Boring small injection ports 210 into the section of infested wood 202 will allow the operator to pump or otherwise dispense killing solution 100 directly into galleries 204 created by the insects. As shown, insects are killed 206 on contact with the killing solution 100, but due to the not highly volatile nature of the aqueous solution, unless in a vapor form, living insects 208 generally will still need to be contacted with the killing solution 100 to result in complete extermination.

It will be understood that the nozzle 110 can be any nozzle means which will deliver killing solution 100 precisely where desired, such as in a wall space, ceiling space, into the galleries of an infested piece of wood, etc. Such nozzle means further include syringes, needles, injectors, pumps, etc. and will be known to those skilled in the art.

It has been observed experimentally that the rate of killing of the insects is often proportional to the concentration of the capsicum containing ingredients in the killing solution. It will be understood, additionally, that the term capsicum as used herein shall serve to include any material containing, but not limited to, capsicum itself, any chemically synthesized or natural extract of any plant of the genus Capsicum, any material containing capsaicin, any of the capsinoids or capsaicinoids, homologs, analogs, derivatives or similar compounds or formulations.

Solvent/Carrier

As described above, the principle solvent for the formulations of the present invention is water. Additional chemicals in the present formulation include surfactants, sticking agents, preservatives or biocidal agents, coloring dyes or agents, fragrance, etc.

In a preferred embodiment, the formulation of the present invention contains mineral oil. In a preferred embodiment, the killing solution contains a sticking agent. In a preferred embodiment, the method for exterminating ants, termites, other pests, including agricultural pests consists of contacting the ants, termites, other pets, or agricultural crops with an aqueous formulation containing capsicum and mineral oil whereby the aqueous formulation is a killing solution. In a preferred embodiment, the concentration of mineral oil in the aqueous solution is about 1%, or more or less. In a preferred embodiment, the concentration of mineral oil in the aqueous solution is about 0.1% or more or less. In a preferred embodiment, the concentration of mineral oil in the aqueous solution is about 10%, or more or less. In a preferred embodiment, the concentration of mineral oil in the aqueous solution is about 90%, or more or less.

Mineral oil has been found to be a preferred additive to the present invention. Use of mineral oil in the formulation enhances dispersion, reduces fogging or misting of a potentially irritating or noxious odor. Mineral oil is non-toxic to humans, and is safe to use in households and other animal and people environments.

Applications

In preferred embodiments of the method and formulations of the present invention, use of a capsicum or other capsaicin-containing solution is effective in sterilizing, as an antimicrobial or sterilizing agent, for use in meat processing plants. These formulations can be used for sterilizing other equipment and food products used in such industries. Reducing the spread of *E. coli,* Salmonella, and other pathogenic bacteria can be very effective when these formulations are used in restaurants, food processing and animal processing areas or facilities.

EXAMPLES

Study 1
The Use of Pepper Extract as a Possible Mortality Agent against Termites

Objective

To determine whether the active ingredients in "Habanero" peppers (assumed to be capsicum) have the ability to kill termites.

Methods

"Habanero" Pepper Solution

Ten medium sized "Habanero" peppers were finally chopped and allowed to soak for three hours in 600 mL. of purified water. The solution was then filtered into a spray bottle for experiments.

Termites 2 termite species, commonly known as drywood and subterranean termites, were collected in the field. Twenty-five drywood termites were divided into two groups: one which contained 14 termites and one which contained 11 termites. Each group of termites was placed in a 9 cm diameter petri dish containing moistened filter paper. The first group containing 14 termites was subjected to three bursts from the spray bottle containing the pepper extract. The second group consisting of 11 drywood termites was subjected to three bursts from a spray bottle containing water only which served as a control. The same experimental design was used for subterranean termites except the treatment and control groups contained 14 and 13 termites, respectively.

Termites were maintained in their respective petri dishes for 24 hours, after which counts were made to determine the number of termites surviving for each group.

Significant differences in survivorship were compared for each species using a x2 test of independence.

Results

Data for subterranean termites are shown below. Thirteen of 14 termites were dead after 24 hrs. when exposed to pepper extract. No termites in the water controlled died in this period. This result is statistically significant based on the following computations:

| Observed | Alive (after 24 hrs.) | Dead (after 24 hrs.) | Totals frequencies |
|---|---|---|---|
| Pepper extract | 1 | 13 | 14 |
| Water control | 13 | 0 | 13 |
| Totals | 14 | 13 | 27 |

From the data we can predict expected frequencies

| Observed | Alive (after 24 hrs.) | Dead (after 24 hrs.) | Totals frequencies |
|---|---|---|---|
| Pepper extract | 7.3 | 6.7 | 14 |
| Water Control | 6.7 | 6.3 | 13 |
| Totals | 14 | 13 | 27 |

The $x^2$ value is calculated below:

$$x^2 = \frac{(|1-7.3|-.50)^2}{7.3} + \frac{(|13-6.7|-.50)^2}{6.7} + \frac{(|13-6.7|-.50)^2}{6.7} + \frac{(|0-6.3|-.50)^2}{6.3}$$

$X^2=19.9$, $df=1$ $x^2$ Table value=7.9 at $p=0.005$

Because the obtained value (19.9) is greater than the table value (7.9), we can conclude that pepper extract is significantly associated with subterranean termite morality. There is only a 0.05% probability that our results were due to chance alone.

Conclusions

Based on this experiment is concluded that "Habanero" pepper extract has the ability to kill subterranean termites under the following controlled laboratory conditions: direct contact with the pepper extract and continuous exposure to this extract for 24 hrs. in a contained environment.

Study 2
The Use of Synthetic Oleoresin as a Possible Mortality and Repellent Agent Against Ants

Objective

To determine whether water soluble oleoresin capsicum has the ability to kill and repel Argentine ants.

Methods

Oleoresin Capsicum Solution

Capsicum solutions were used for this experiment prepared by adding 5 and 20 mL of capsicum (250,000 scoval units) t0 45 and 30 mL of water to make solutions of 10% and 40% capsicum, respectively.

Mortality Tests

The Argentine ant (*Irdomyrnex humilis*) were collected in the field. At least 30 individual ants were placed in a 9 cm. diameter petri dish containing filter paper. Fluon was painted on the sides of dishes to prevent escape. Ants were then subjected to three bursts from a spray bottle containing the 10% capsicum extract. A similar petri dish with ants was prepared and sprayed with distilled water as a control. This experiment was then repeated using the 40% solution. Ants were maintained in their respective petri dishes for 1 hour, after which counts were made to determine the number of ants surviving for each group. Significant differences in survivorship were compared for each species using Fisher's extract test of independence.

Results

| Subjects | Alive | Dead | |
|---|---|---|---|
| Fisher Exact Test Ants 10% | | | |
| Row 1 | 30.000 | 3.000 | Counts |
| | 12.375 | 20.625 | Expected Counts |
| | 90.909 | 9.091 | Row % |
| | 100.000 | 6.000 | Column % |
| | 37.500 | 3.750 | Total % |
| Row 2 | 0.000 | 47.000 | Counts |
| | 17.625 | 29.375 | Expected Counts |
| | 0.000 | 100.000 | Row % |
| | 0.000 | 94.000 | Column % |
| | 0.000 | 58.750 | Total % |
| Fisher Exact Test Ants 40% | | | |
| Row 1 | 30.000 | 0.000 | Counts |
| | 11.538 | 18.462 | Expected Counts |
| | 100.000 | 0.000 | Row % |
| | 100.000 | 0.000 | Column % |
| | 38.462 | 0.000 | Total % |
| Row 2 | 0.000 | 48.000 | Counts |
| | 18.462 | 29.538 | Expected Counts |
| | 0.000 | 100.000 | Row % |
| | 0.000 | 100.000 | Column % |
| | 0.000 | 61.538 | Total % |

The proportion of observations in the different categories which define the contingency table is significantly different than is expected from random occurrence (P=0.001)

Conclusions

Few ants died when subjected to water alone in both experiments. However, all ants subjected to both capsicum solutions died within minutes of exposure. There was a significant difference between treatments and controls indicating that capsicum at these concentrations is lethal to Argentine ants.

Study 3
The Use of Oleoresin Capsicum as a Possible Mortality Agent against Dampwood Termites

Objective

To determine whether water soluble oleoresin capsicum kills dampwood termites

Methods

Oleoresin Capsicum Solution

Dried fruit of Capsicum frutescens and/or *C. Annuum* measured at 500,000 Scoville heat units

Mortality Tests

Dampwood termites (Zootermopsis spp.) were collected in a field. Twenty individual termites were placed in a 9 cm. diameter petri dish containing filter paper. Termites were then subjected to three bursts from a spray bottle containing the capsicum extract. A similar petri dish with termites was prepared and sprayed with distilled water as a control. Termites were maintained in their respective petri dishes for each group. Significant differences in survivorship were compared using a chi-square test.

Results

Data for dampwood termites are shown below.

| | Alive (after 24 hrs.) | Dead (after 24 hrs) | Totals frequencies |
|---|---|---|---|
| Observed | | | |
| Pepper extract | 0 | 20 | 20 |
| Water control | 20 | 0 | 20 |
| Totals | 20 | 20 | 40 |
| From this data we can predict expected frequencies | | | |
| Expected | | | |
| Pepper extract | 10 | 10 | 20 |
| Water control | 10 | 10 | 20 |
| Totals | 20 | 20 | 40 |

The $x^2$ value is calculated below:

$$x^2 = \frac{(|0-10|-.50)^2}{10} + \frac{(|20-10|-.50)^2}{10} + \frac{(|20-10|-.50)^2}{10} + \frac{(|0-10|-.50)^2}{10} = 36.1$$

Formula, table values, and computations can be found in Biometry, by Sokal and Rolf $X^2$=36.1, $df$=1

$x^2$ Table value=7.9 at $p$=0.005

Because the obtained value (36.1) is greater than the table value (7.9), we can conclude that water soluble oleoresin capsicum is significantly associated with dampwood termites mortality.

Conclusions

Dampwood termites exposed to water soluble oleoresin capsicum at a concentration of 500,000 scoval units were killed on contact.

Study 4
The Use of Oleoresin Capsicum as a Possible Mortality Agent against Odorous House Ants

Objective

To determine whether water soluble oleoresin capsicum kills odorous house ant

Methods

Oleoresin Capsicum Solution

Dried fruit of *Capsicum frutescens* and/or *C. Annuum* measured at 500,000 Scoville heat units

Mortality Tests

Odorous house ants (Tapinoma spp.) were collected in the field. Twenty individual ants were placed in a 9 cm. diameter petri dish containing filter paper. Fluon was painted on the sides of dishes tp prevent escape. Ants were then subjected to three bursts from a spray bottle containing the capsicum extract. A similar petri dish with ants was prepared and sprayed with distilled water as a control. Ants were maintained in their respective petri dishes for 1 hour, after which counts were made to determine the number of ants surviving for each group. Significant differences in survivorship were compared using a chi-square test.

Results

Data for odorous house ants are shown below.

|  | Alive (after 24 hrs.) | Dead (after 24 hrs) | Totals frequencies |
|---|---|---|---|
| Observed |  |  |  |
| Oleoresin capsicum | 0 | 20 | 20 |
| Water control | 20 | 0 | 20 |
| Totals | 20 | 20 | 40 |
| From this data we can predict expected frequencies |  |  |  |
| Expected |  |  |  |
| Oleoresin capsicum | 10 | 10 | 20 |
| Water control | 10 | 10 | 20 |
| Totals | 20 | 20 | 40 |

The $x^2$ value is calculated below:

$$x^2 = \frac{(|0-10|-.50)^2}{10} + \frac{(|20-10|-.50)^2}{10} + \frac{(|20-10|-.50)^2}{10} + \frac{(|0-10|-.50)^2}{10} = 36.1$$

Formula, table values, and computations can be found in Biometry, by Sokal and Rolf $X^2 = 36.1$, $df=1$ $x^2$ Table value=7.9 at $p=0.005$

Conclusions

Because the obtained value (36.1) is greater than the table value (7.9), we can conclude that water soluble oleoresin capsicum is significantly associated with odorous house ant mortality. Odorous house ants exposed to water soluble oleoresin capsicum at a concentration of 500,000 scoval units were killed on contact.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

I claim:

1. A method for exterminating ants consisting of contacting the ants with an aqueous formulation containing capsicum whereby the aqueous formulation is a killing solution.

2. The method of claim 1 in which the step of contacting the ants with an aqueous formulation containing capsicum includes injecting said killing formulation into infested wall portions of an existing structure.

3. The method of claim 1 in which the step of contacting the ants with an aqueous formulation containing capsicum includes injecting said killing formulation into and around infested foundation portions of an existing structure.

4. The method of claim 1 in which the step of contacting the ants with an aqueous formulation containing capsicum includes injecting said killing formulation into the soil adjacent an infestation of an existing structure.

5. The method of claim 1 in which the step of contacting the ants with an aqueous formulation containing capsicum includes delivering the killing formulation to saturate an area adjacent an infestation.

6. The method of claim 1 in which the step of contacting the ants with an aqueous formulation containing capsicum includes spraying pressurized killing formulation to coat an area adjacent an infestation with liquid killing solution.

7. The method of claim 1 in which the step of contacting the ants with an aqueous formulation containing capsicum includes forming a vapor out of the killing formulation and transporting the vapor to an infested area.

8. The method of claim 7 in which the vapor is formed by boiling the aqueous formulation.

9. The method of claim 7 further including the step of injecting the vapor underneath a barrier covering the infested area.

10. The method of claim 7 in which the vapor is formed by injecting the killing formulation through an aerosol forming nozzle.

11. A method for exterminating termites consisting of contacting the termites with an aqueous formulation containing capsicum whereby the aqueous formulation is a killing solution.

12. The method of claim 11 in which the step of contacting the termites with an aqueous formulation containing capsicum includes injecting said killing formulation into infested wall portions of an existing structure.

13. The method of claim 1 in which the step of contacting the termites with an aqueous formulation containing capsicum includes injecting said killing formulation into and around infested foundation portions of an existing structure.

14. The method of claim 1 in which the step of contacting the termites with an aqueous formulation containing capsicum includes injecting said killing formulation into the soil adjacent an infestation of an existing structure.

15. The method of claim 1 in which the step of contacting the termites with an aqueous formulation containing capsicum includes delivering the killing formulation to saturate an area adjacent an infestation.

16. The method of claim 1 in which the step of contacting the termites with an aqueous formulation containing capsicum includes spraying pressurized killing formulation to coat an area adjacent an infestation with liquid killing solution.

17. The method of claim 1 in which the step of contacting the termites with an aqueous formulation containing capsicum includes forming a vapor out of the killing formulation and transporting the vapor to an infested area.

18. The method of claim 17 in which the vapor is formed by boiling the aqueous formulation.

19. The method of claim 17 further including the step of injecting the vapor underneath a barrier covering the infested area.

20. The method of claim 17 in which the vapor is formed by injecting the killing formulation through an aerosol forming nozzle.

* * * * *